(12) United States Patent
Shih et al.

(10) Patent No.: US 8,414,875 B2
(45) Date of Patent: Apr. 9, 2013

(54) BAIT FOR HUMID REGIONS

(75) Inventors: Cheng-Jen Shih, Taipei (TW); Lekhnath Kafle, Taipei (TW)

(73) Assignee: National Taiwan University, Taipei (TW)

( * ) Notice: Subject to any disclaimer, the term of this patent is extended or adjusted under 35 U.S.C. 154(b) by 120 days.

(21) Appl. No.: 12/628,376

(22) Filed: Dec. 1, 2009

(65) Prior Publication Data
US 2011/0047861 A1 Mar. 3, 2011

(30) Foreign Application Priority Data
Sep. 3, 2009 (TW) .............................. 98129695 A

(51) Int. Cl.
*A01N 25/00* (2006.01)
*A01M 7/00* (2006.01)
*A01M 17/00* (2006.01)

(52) U.S. Cl. ........................................ 424/84; 43/132.1

(58) Field of Classification Search .................. None
See application file for complete search history.

(56) References Cited

U.S. PATENT DOCUMENTS

| 4,756,118 A | 7/1988 | Evans, II |
| 4,874,611 A | 10/1989 | Wilson et al. |
| 5,031,355 A | 7/1991 | Ryan |
| 5,054,231 A | 10/1991 | Witherspoon |
| 5,165,199 A | 11/1992 | Tallon |
| 6,026,609 A | 2/2000 | Rawls |
| 6,566,392 B1 * | 5/2003 | Okada et al. .................. 514/461 |
| 2008/0249190 A1 * | 10/2008 | Jensen et al. .................. 514/777 |

FOREIGN PATENT DOCUMENTS

| TW | I262763 | 5/2005 |
| TW | I264286 | 9/2005 |

OTHER PUBLICATIONS

James T. Vogt et al., Effects of Temperature and Season on Foraging Activity of Red Imported Fire Ants (Hymenoptera: Formicidae) in Oklahoma, Environ. Entomol. 32(3), 2003, 447-451.
Lekhnath Kafle et al., Microencapsulated Bait: Does It Work With Red Imported Fire Ants, *Solenopsis invicta* (Hymenoptera: Formicidae)?, Sociobiology, vol. 53, No. 3, 2009, 729-737.
Furman, B.D. et al., Determination of the Most Effective Chemical Form and Concentrations of Indoxacarb, as well as the Most Appropriate Grit Size, for use in Advion, Sociobiology 48: 309-333, 2006.
Jian Chen, Advancement on techniques for the separation and maintenance of the red imported fire ant colonies, Insect Science, vol. 14, 2007, 1-4.
Lekhnath Kafle et al., Simplified approaches to determine the attractant preference of *Solenopsis invicta* (Hymenoptera: Formicidae), Appl. Entomol. Zool. 43 (3), 2008, 383-390.
Lekhnath Kafle et al., Effect of Surfaces on the Foraging Efficiency of *Solenopsis invicta* (Hymenoptera: Formicidae), Formosan Entomol., 29, 2009, 51-58.

* cited by examiner

*Primary Examiner* — Daniel Sullivan
*Assistant Examiner* — Kyle Purdy
(74) *Attorney, Agent, or Firm* — WPAT, P.C.; Anthony King

(57) ABSTRACT

The present invention is related to bait which is water resistance, especially for fire ants. Its water resistance, anti-oxidation and the use of fire ants favorite eating formula which can mix with different toxic substances, and the production is easy and low cost, suitable for use in Taiwan or other humid areas to control fire ants.

10 Claims, 2 Drawing Sheets

BAIT FOR HUMID REGIONS

FIELD OF THE INVENTION

The present invention relates to development a water resistant and anti-oxidant bait, which is suitable for use in humid areas to control fire ants.

BACKGROUND OF THE INVENTION

Since their accidental introduction to Taiwan in 2003 the red imported fire ants, *Solenopsis invicta* Buren (Hymenoptera: Formicidae) have become an important economic, agricultural, as well as a local biodiversity and public health problem in both rural and urban areas. Several techniques are being used around the world either to control the fire ant population or to limit their further expansion. To control *S. invicta* over a larger area, toxic bait products are the most effective tool (Vogt et al., Environ. Entomol. 32: 447-451, 2003).

The ant baits are prepared with three major components, a toxicant, a vegetable oil as a phagostimulant, and a carrier (usually corn grits) for the phagostimulant/toxicant solution to allow easy distribution of the bait and to let fire ants carry baits back to their nests to feed larvae and gyne to reach the purpose of killing gyne. The bait should be fresh and tasty so that it can attract fire ants to carry it into their nests. However, the drawback of commercial bait is that when it exposes to a humid place, it is easily to break down. Moreover, after keeping commercial bait in water for 0.5 hour, it becomes attached to each other forming a single soft ball, and the chemical properties of the vegetable oil used as an attractant could be destroyed. Therefore, there is a strong market demand for the development of a high humidity or water resistant ant bait that can make the viability of ant bait less dependent upon good weather, even can be used when raining days. The humid resistant ant bait is especially useful at humid places such as Taiwan, Hong Kong or mainland China, because in these areas, basically there has not many days to carry out the fire ant control programs determined by it does not rain. Therefore, developing bait for humid regions plays an important role in control fire ants (Kafle et al., Sociobiology 53: 729-737, 2009).

Some attempts have been made to develop moisture resistant ant bait by coating the corn grit carrier by microencapsulation using existing coating material (Kafle et al., Sociobiology 53: 729-737, 2009) or by finding a new coating material or new carrier. However, Kafle et al. (Kafle et al., Sociobiology 53: 729-737, 2009) reported that although microencapsulated corn grit bait could resist water, the ants were not stimulated to feed on them. U.S. Pat. No. 4,874,611 discloses a microencapsulated ant bait. It uses a gelling agent such as carrageenan and the attractant were added to the shell. Even though it can also be water-resistant, but the cost is high, and the producing is inconvenient. Thus, using microencapsulation may not be a suitable alternative towards the development of a high humidity or water resistance fire ant bait.

In addition to bait development and improvement, TW patent number I262763 discloses an ant feeding device, comprising a tube body and a combination piece, wherein the tube body has a capacity to place bait, and the capacity has a hole. The combination piece combines the tube body, and has a block piece corresponding to the hole in order to block or partial block the hole to supply the bait quantitatively. The combination piece can be inserted into ground, making the hole maintain appropriate distance from the ground to avoid the bait getting wet.

There are also several methods and devices to eradicate fire ants at present. One of them is by inserting a tip of the lance assembly into a Solenopsis infested mound and then delivering vaporized insecticides in to the mound by the lance to eradicate fire ants (U.S. Pat. No. 4,756,118). Another method is to drench the whole fire ant mound with water and insecticide mixture (U.S. Pat. No. 5,054,231). The above two methods all need to contact drugs or aqueous solution containing insecticides with gyne and fire ants to achieve the desired effect. In particular, some fire ants bury the gyne into the ground below one meter, and it is difficult to let the drugs or aqueous solution containing insecticides to go into such a deep place, and this method has the risk of environmental pollution.

Another way to kill fire ants is by using a tent covering the ant mound and injecting vapor gas to the ant mound (U.S. Pat. No. 5,031,355). Recent development is to use a probe injecting hot steam into ant mound to kill fire ants (U.S. Pat. No. 6,026,609). The above two methods are major in using the heat steam to kill fire ants. The disadvantage is that when the steam jets into ant mound, it would condense into drops and block the access. The follow-up steam can not be sustained jet into the bottom of the ant mound so that it can not eradicate fire ants completely. It needs using this method several times to achieve the desired effect. Using refrigerant or coolant such as liquid nitrogen is also a way to kill fire ants (U.S. Pat. No. 5,165,199). Using liquid nitrogen to kill fire ants is by its low-temperature $-196°$ C. to freeze fire ants. Although the effect of this method is good, the low temperature of liquid nitrogen is not easy to carry and operate, and it requires specific equipment of thermal insulation tank and pipe to store and transfer the liquid nitrogen before injecting into the fire ant mound. Because the complicating equipment, cumbersome operation, high-cost of liquid nitrogen and the inconvenience of economy and use, making universal use of this method difficult. It had also used hot air spraying on indoor carpet to eradicate insects and other tiny organisms. This method is effective for insects and other tiny organisms which expose to outside, but it is useless for red fire ants which are deep in the underground. Taiwan Patent No. I264286 discloses fire ant eradication device using high-pressure heated gas pulses and method thereof. The device and method for killing fire ants are by introducing of high-pressure hot gas pulses to the fire ant mound. A metal hollow probe having a plurality of orifice near its bottom is mechanically or manually inserted into fire ant mound. Hot gas in the metal hollow probe is ejected in pulse into the ant mound from the orifices, through channels in the ant mound, whereby hot gas is filled in the whole ant mound rapidly, heating and killing the fire ants and ant queens before they move to safety. Although the above mentioned methods can eradicate fire ants, the equipments and materials of these methods are not available on the market, and the operation may be complicated and dangerous.

SUMMARY OF THE INVENTION

The present invention provides a water resistant and anti-oxidant bait formula, comprising: (a) an effective amount of toxicant, (b) an attractant, (c) shrimp shell powder, and (d) distiller's dried grains with solubles (DDGS) as a carrier.

The present invention further provides a method of killing pest, comprising spreading the bait formula of the present invention to attract the pest to eat or to transport the bait formula into mound to feed the pest.

DETAILED DESCRIPTION OF THE INVENTION

Figure 1:
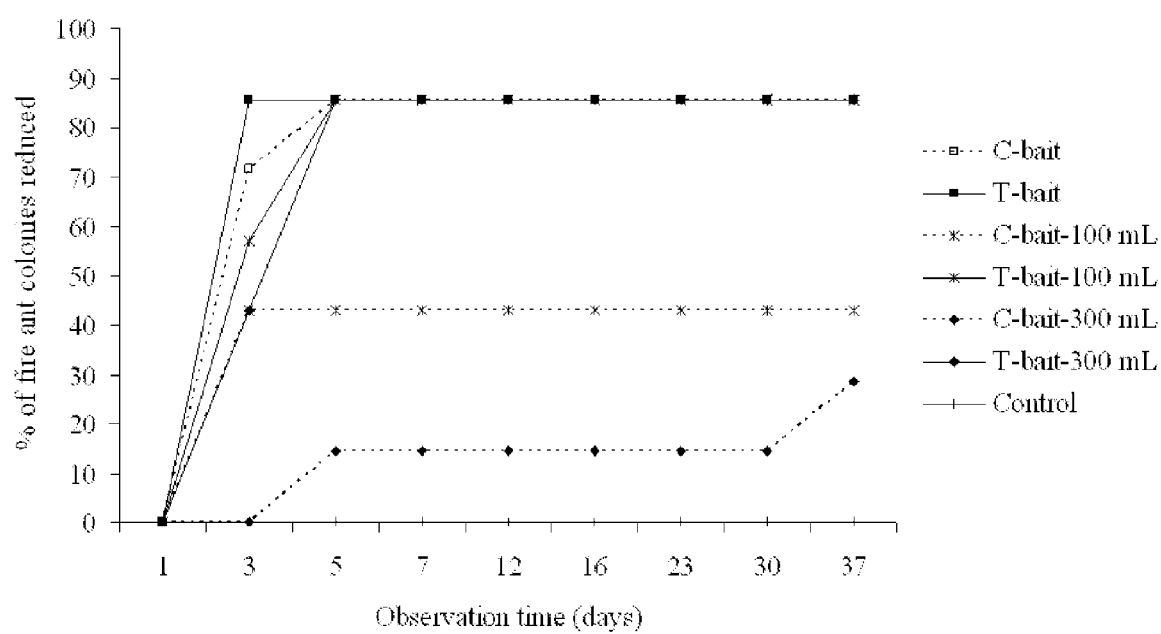
FIG. 1 Rates of fire ant colonies reduction by fire ant baits with different volume of water sprayed under field conditions.
Figure 2:
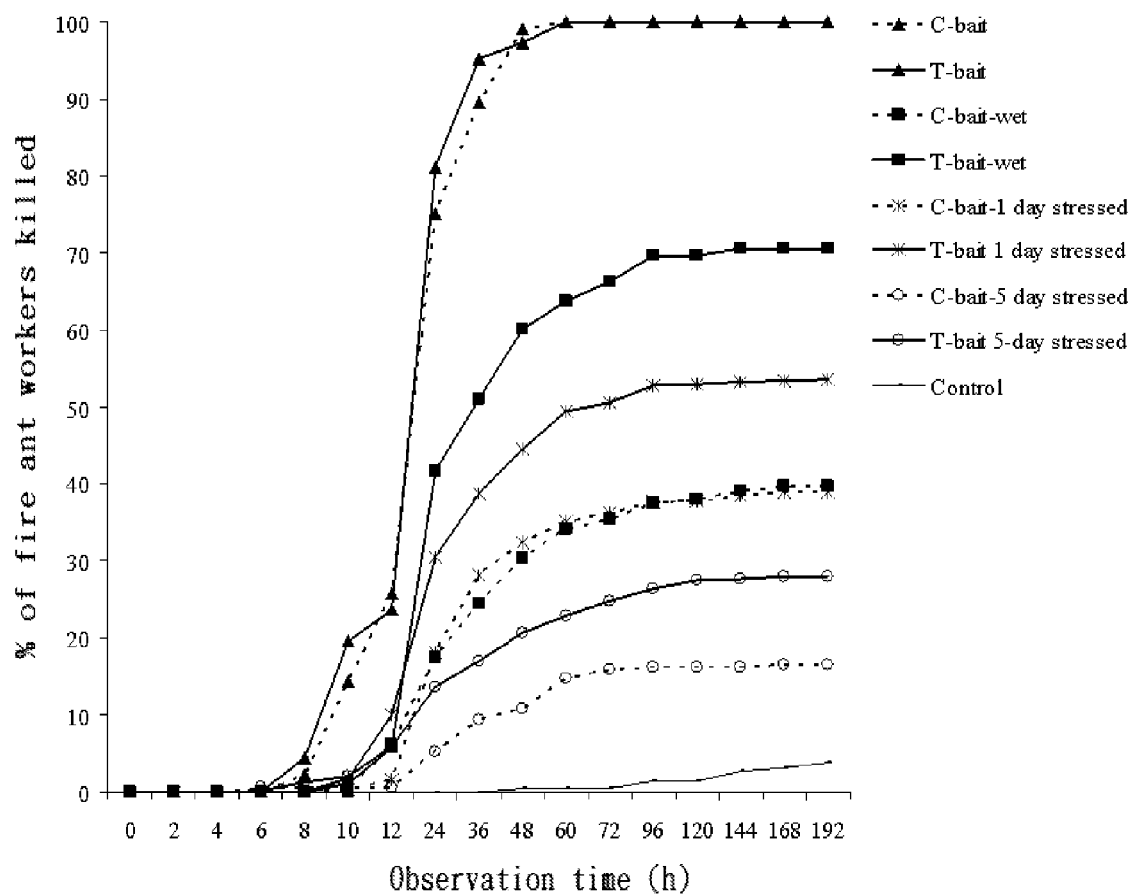
FIG. 2 Percentage of fire ant workers killed by normal, wet and environmentally stressed baits under laboratory conditions.

In order to solve the above mentioned problems that the baits can't be resistant to moisture, oxidation caused by environmental stress, or complicated methods of killing fire ants, the present invention provides a water resistant and antioxidant bait formula, comprising: (a) an effective amount of toxicant, (b) an attractant, (c) shrimp shell powder, and (d) distiller's dried grains with solubles (DDGS) as a carrier. The bait is suitable for humid areas, such as Taiwan, Hong Kong or mainland China, etc. It is specific for outside to ant control programs, especially for fire ant.

The bait of the present invention uses distiller's dried grains with solubles (DDGS) as a carrier, said carrier of DDGS which does not like the commercial carrier of corn grit that is easily to form a single soft ball, hard to preserve, and loss the preference by fire ant so that it can not achieve the goal of killing fire ants when wetted. The DDGS as a carrier of the present invention can mix with many kinds of pesticides, growth regulators or toxicants for different programs of controlling pests. The present invention can be used to control pests, which include but are not limited to cockroaches, ants, termites, fire ants, or similar arthropod pests. In a preferable embodiment, it is used to control fire ants.

The toxicant of the present invention includes but is not limit to the following materials as pesticides: abamectin, acephate, acetamiprid, acrinathrin, alanycarb, aldicarb, allethrin, alpha-cypermethrin, aluminium phosphide, amitraz, azadirachtin, azamethiphos, azinphos-ethyl, azinphos-methyl bendiocarb, benfuracarb, bensultap, beta-cyfluthrin, beta-cypermethrin, bifenthrin, bioallethrin, S-cyclopentenyl isomer, bioresmethrin, bisatrifluron, borax, buprofezin, butocarboxim, butoxycarboxim, cadusafos, calcium cyanide, calcium polysulfide, carbaryl, carbofuran, carbosulfan, cartap, chlordane, chlorethoxyfos, chlorfenapyr, chlorfenvinphos, chlorfluazuron, chlormephos, chloropicrine chlorpyrifos, chlorpyrifos-methyl, chromafenozide, clothianidin, coumaphos, cryolite, cyanophos, cycloprothrin, cyfluthrin, cyhalothrin, cypermethrin, cyphenothrin, cyromazine, dazomet, deltamethrin, demeton-S-methyl, diafenthiuron, diazinon, dichlorvos, dicrotophos, dicyclanil, diflubenzuron, dimethoate, dimethylvinphos, dinotefuran, disulfoton, emamectin, emamectin benzoate, empenthrin, endosulfan, esfenvalerate, ethiofencarb, ethion, ethiprole, ethoprophos, ethylene dibromide, etofenprox, etoxazole, famphur, fenitrothion, fenobucarb, fenoxycarb, fenpropathrin, fenthion, fenvalerate, fipronil, flonicamid, flucycloxuron, flucythrinate, flufenoxuron, flumethrin, formetanate, formetanate hydrochloride, fosthiazate, furathiocarb, halofenozide, heptachlor, heptenophos, hexaflumuron, hydramethylnon, hydroprene, imidacloprid, imiprothrin, indoxacarb, isofenphos, isoprocarb, o-(methoxy-amino-thiophosphate) isopropyl salicylate, isoxathion, lambda-cyhalothrin, PFOS, lufenuron, magnesium phosphide, malathion, mecarbame, dimercury dichloride, metam, metam-sodium, methamidophos, methidathion, methiocarb, methomyl, methoprene, methothrin, methoxychlor, methoxyfenozide, methyl isothiocynate, metalcarb, mevinphos, milbemectin, monocrotophos, naled, naphthalenic compounds, nicotine, nitenpyram, nithiazine, novaluron, noviflumuron, omethoate oxamyl, oxydemeton-methyl, parathion, methyl parathion, pentachlorophenol, pentachlorobenzene dodecanoate, permethrin, petroleum oils, phenothrin, phenthoate, phorate, phosalone, phosmet, phosphamidon, phosphine, phoxim, pirimicarb, pirimiphos-methyl, prallethrin, profenofos, propaphos, propetamphos, propoxur, prothiofos, pymetrozine, pyraclofos, pyrethrins, pyridaben, pyridaphenthion, pyrimidifen, pyriproxyfen, quinalphos, resmethrin, rotenone, sabadilla, silafluofen, sodium cyanide, pentachlorobenzene sodium oxide, spinosad, sulcofuron, sulcofuron-sodium, sulfluramid, sulfotep, sulfuryl fluoride, sulprofos, tau-fluvalinate, tebufenozide, tebupirimfos, teflubenzuron, tefluthrin, temephos, terbufos, tetrachlorvinphos, tetramethrin, theta-cypermethrin, thiacloprid, thiamethoxam, thiodicarb, thiofanox, thiometon, thiosultap-sodium, tolfenpyrad, tralomethrin, transfluthrin, triazamate, triazophos, trichlorfon, triflumuron, trimethacarb, vamidothion, xylylcarb, zeta-cypermethrin, and zinc phosphide. The more preferable toxicants are d-Allethrin, cypermethrin, permethrin, and pyrethrin, and the most preferable toxicant is cypermethrin. The most effective amount of toxicant is 0.128% cypermethrin.

The attractant of the present invention, for example, can be fat and oil, such as solid oil, like butter, lard, margarine, or other shortening creams, or can also be liquid oil. It can also be alcohols, such as Shaoxing ricewine, beer, or wine; or be vinegar, such as black vinegar, red vinegar, drinking vinegar. It can also be extract of variety fruits, fermentation of fruits or vegetables, miso, yeast, honey, liquid sugar, brown sugar, vegetable or animal prey agents. In the circumstance of not affecting the attractive nature, the attractant can be added with a variety of pesticides to give the effect of insecticide. In a preferable embodiment of the present invention, the attractant is oil, and the more preferable attractant is vegetable oil, the most preferable attractant is soybean oil.

Another feature of the present invention is that is adds shrimp shell powders (SSP) as a phaostimulant. Even when the oil's chemical properties are destroyed by water, the SSP remains active in attracting fire ants and stimulating them to feed on wet baits. In a preferable embodiment, the bait having a weight ration of shrimp shell powder to DDGS from 1:10 to 2:9, and in the most preferable embodiment, the bait having a weight ration of shrimp shell powder to DDGS is 1:5.

The present invention further provides a method of killing pest, comprising spreading the bait formula of the present invention outdoor to attract the pest to feed on them. Said outdoor comprising areas which the pest living or prowling (such as plants, fields, forests, orchards, waterways, soil, plant products, etc.) or areas which is vulnerable infected by pests in the future. Therefore, the present invention can be conducive to practical use, such as agricultural, horticultural crops, forestry, veterinary medicine, livestock or public health.

EXAMPLE

The examples below are non-limiting and are merely representative of various aspects and features of the present invention.

Example 1

T-bait (Cypermethrin) Preparation

T-carrier

To prepare T-bait, distiller's dried grains with solubles (DDGS) was used as a carrier (T-carrier) bought from a local market. The DDGS was first screened through a laboratory sieve with a #9 mesh (2 mm) followed by a #12 mesh (1.4 mm) to end up with standard sized particles of ~2 mm (Furman, B. D. et al., Sociobiology 48: 309-333, 2006). The screened DDGS particles were then stored in the refrigerator for future use. The DDGS are the dried residue remaining after the starch fraction of corn is fermented with selected yeasts and enzymes to produce ethanol and carbon dioxide.

After complete fermentation, the alcohol is removed by distillation and the remaining fermentation residues are dried.

Toxicants

The cypermethrin (94%) obtained from a local chemical company (Chung Shi Chemical Plant, Hsinchu, Taiwan) was used as the toxicant in the present invention. A stock solution of 2% AI was prepared by mixing 1.08 mL cypermethrin (94%) with 50 mL acetone and stored in the refrigerator for future use.

Soybean Oil as an Attractant and Shrimp Shell Powder as a Phagostimulant

In the present invention, the soybean oil and other ingredients were used as attractants, and SSP was used as a phagostimulant of the T-bait. 15 or 20% soybean oil (by wt.) and 20% SSP (by wt.) mixed with T-carriers attracted the highest number of fire ant workers compared to any of the other combinations. In a preferable embodiment, 15% of soybean oil (by wt.) and 20% SSP powder (by wt.) were mixed with T-carriers to prepare the T-bait.

To prepare SSP, dry shrimp shells bought from a local market and grinded to fine powders. The grinded powders were screened through a fine sieve to end up with very fine SSP. The screened SSP were then stored in the refrigerator for future use.

The method of preparing T-bait with cypermethrin (0.128%) as the toxicant are described below: 6.35 mL of the prepared and stored stock solution as described at previous section, was mixed with 15 mL of soybean oil and shaken until well mixed with the oil. Then 100 g T-carrier was mixed with 20 g of SSP powder followed by that mixture put in a "Stirrer" (KM-416, Kenwood Ltd, UK) and mixed at 220 revolutions per minute (rpm) for 15 min. During those 15 min, the above-mentioned soybean oil and cypermethrin in acetone mixture was dropped slowly into the "Stirrer" containing the T-carrier and the SSP powder. In 15 min, the adding of the oil mixture was completed and the mixing speed was reduced to 110 rpm for the next 45 min. After a total of 1 h of mixing, the prepared T-bait cypermethrin (0.128%) was then packed in airtight plastic bags and stored in a refrigerator for future use. T-bait blank, T-bait without toxicant used in this study as a "control" was prepared following the same procedures as T-bait.

Example 2

Efficacy of T-Bait (0.128% Cypermethrin) and C-Bait in the Laboratory

C-bait

The Commercial Bait (C-Bait), "Advion" (Indoxacarb 0.045% Ai) (Dupont Professional Products, USA) used in this invention was obtained from the National Red Imported Fire Ant Control Center, Taiwan.

Source of S. invicta

Solenopsis invicta colonies were collected from Hsinchu County, Taiwan, separated from the soil by water drip method (Chen J, Insect Sci. 14: 1-4, 2007), and reared under laboratory conditions as described by Kafle et al. for at least one week prior to conducting the experiments Kafle et al. (Kafle et al., Appl. Entomol. Zool. 43: 383-390, 2008; Kafle et al., Formosan Entomol. 29: 51-58, 2009). Laboratory ants were starved 2 days prior to the experiment to ensure that their mid-gut was empty and that they were hungry enough to search for food (Furman et al., Sociobiology 48: 309-333, 2006).

Foraging Area, Nest Preparation and Bait Placement

A rectangular artificial foraging area, measuring 18.5 cm×10.5 cm and 4 cm high was used for the present invention. To prevent the ants from escaping, the inside of the walls of the enclosure were coated with Fluon™ (NP115; Northern Products, Inc., Woonsocket, R.I.). The artificial nest was placed 1 cm away from the inner wall of the container. The layout details of artificial nest are as per Kafle et al. (Appl. Entomol. Zool. 43: 383-390, 2008). Formulated bait (ca. 1 g) was kept on the half cut plastic weighing plate and placed ~10 cm away from the artificial nest.

Method of Evaluating the Efficacy of T-Bait (0.128% Cypermethrin) and C-Bait in the Laboratory To determine the toxicity of T-bait (0.128% Cypermethrin) and C-bait to the fire ants, a method reported by Oi, D. H. et al., J. Econ. Entomol. 99: 1739-1748, 2006 was used with some modifications. About 2000 fire ant workers (1.11 g) and 400 broods (0.25 g) were obtained from the laboratory colonies and were starved for 2 days. A total of 100 ants and 20 broods were then transferred to the artificial foraging area with artificial nests as described in the previous section and held overnight. The next day, any dead ants were replaced with ants from the starved populations.

A half cut plastic weighing plate filled with bait (ca 1 g) was placed into each container containing the ants. After 24 h, the weighing plates containing the bait were removed and the ants were held without food for an additional 24 h to allow for any trophallactic exchange of toxicant. Next, a mealworm larva (Tenebrio molitor (L.) and water in a tube as the food and water source were added for the remainder of the study. Dead ants were counted and removed after 2, 4, 6, 8, 10, 12, 24, 36, 48, 60, 72, 84, 96, 120, 144, 168 and 192 h after treatment (HAT). This study was replicated four times with ants from a separate colony being used for each replicate.

The experiments were conducted under ambient temperature and relative humidity, which averaged 27±1° C. and 50±3% RH with 14 h light and 10 h dark condition. Means were compared by using SNK test of SAS (2008) and lethal times ($LT_{50}$), the time (days) required for 50% of the ants to die was estimated from Probit analysis using StatPlus (2008).

Result

The number of fire ants killed by normal T-bait and C-bait were not significantly different during all the observations. However the number of fire ants killed by normal T-bait or C-bait were significantly higher than the control during all the observations except at 12 HAT (F=144, P=0.28). At the 96 HAT, all ants were killed by normal T-bait or C-bait. The $LT_{50}$ of normal T-bait and C-bait were 0.69 and 0.74 d, respectively (Table 1).

TABLE 1

Mean number of fire ant workers killed by normal T-bait (0.128% cypermethrin), C-bait (0.045% indoxacarb) and control

| Time (H) | T-bait (Mean ± SE)[a] | C-bait (Mean ± SE)[a] | Control (Mean ± SE)[a] |
|---|---|---|---|
| 12 | 23.72 ± 15.17a | 25.72 ± 18.29a | 0 ± 0a |
| 24 | 81.16 ± 7.82a | 75.03 ± 9.4a | 0 ± 0b |
| 48 | 97.25 ± 2.75a | 99 ± 1a | 0 ± 0b |
| 96 | 100 ± 0a | 100 ± 0a | 0.75 ± 0.48b |
| 192 | 100 ± 0a | 100 ± 0a | 1.75 ± 0.63b |
| $LT_{50}$[b] | 0.69 | 0.74 | |

[a]Means within the same row followed by the same letter are not significantly different (P < 0.05) using SNK test of SAS (2008).
[b]$LT_{50}$ values (in days) were determined by probit analysis (StatPlus, 2008).

Example 3

Efficacy of Wet T-Bait (0.128% Cypermethrin) and C-Bait in the Laboratory

Preparation of Wet Baits

A 50 mL test tube was modified by making a 3 mm dia. hole in the centre of the tube and four 2 mm dia. holes in the bottom of the tube. T-bait or C-bait (ca. 1 g) was transferred to the modified tube, then capped well and turned upside down. After that, 15 mL of DD-water was injected through the hole made in the centre of the tube. The water was kept in the tube for 30 min. After 30 min, the tube was turned right side up again and placed in a test tube rack allowing the water to drain out through the four holes made at the bottom for 15 min. Then the wetted baits were used to determine their toxicity to the fire ants.

Method of Evaluating the Efficacy of Wet T-Bait (0.128% Cypermethrin) and Wet C-bait in the Laboratory The method of evaluating the efficacy in the laboratory was the same as Example 2, but the T-bait (Cypermethrin) and C-bait were replaced with wet T-bait (0.128% Cypermethrin) and wet C-bait, respectively.

Result

The number of fire ants killed by wet T-bait were significantly higher than those killed with wet C-bait at 24, 48, 96 and 192 HAT. However, the number of fire ants killed by wet T-bait or wet C-bait were not significantly different at 12 HAT (F=3.8, P=0.04). The numbers of fire ants killed by wet T-bait or wet C-bait were significantly higher than killed with the control during all the observations. At the final observation at 192 HAT, the highest total number of fire ants killed were by wet T-bait (70.62±2.94%) which was 43.81% and 97.52% more than with the wet C-bait and the control, respectively (F=167.07, P=0.001). The $LT_{50}$ of wet T-bait and wet C-bait were 2.1 and 8.22 d, respectively (Table 2).

TABLE 2

Mean number of fire ant workers killed by wet T-bait (0.128% cypermethrin), wet C-bait (0.045% indoxacarb) and control

| Time (H) | T-bait (Mean ± SE)[a] | C-bait (Mean ± SE)[a] | Control (Mean ± SE)[a] |
|---|---|---|---|
| 12 | 5.65 ± 2.52a | 6.13 ± 2.42a | 0 ± 0b |
| 24 | 41.60 ± 5.94a | 17.48 ± 2.99b | 0 ± 0c |
| 48 | 60.15 ± 4.01a | 30.37 ± 1.74b | 0 ± 0c |
| 96 | 69.71 ± 3.10a | 37.45 ± 1.30b | 0.75 ± 0.48c |
| 192 | 70.62 ± 2.94a | 39.68 ± 2.85b | 1.75 ± 0.63c |
| $LT_{50}$[b] | 2.1 | 8.22 | |

[a]Means within the same row followed by the same letter are not significantly different (P < 0.05) using SNK test of SAS (2008).
[b]$LT_{50}$ values (in days) were determined by probit analysis (StatPlus, 2008).

Example 4

Efficacy of Environmentally Stressed T-Bait (Cypermethrin) and C-bait in the Laboratory Environmentally Stressed Baits To determine the effects of environmental stresses (sunshine exposure, air oxidation and wet-dry cycles) on the efficacy of T-bait (cypermethrin) and C-bait, the environmentally stressed baits were produced by the following method: T-bait (cypermethrin) and C-bait were placed in an open area with sunshine for 6 h and then transferred to the laboratory for 18 h. To expose the baits to the environment, 100 g of T-baits (cypermethrin) and C-baits were kept in a 15 cm dia. Petri dish and placed in a circular container, 40 cm dia.×17 cm high. To prevent the ants from reaching the baits Fluon™ was coated on the outer vertical surface of the container. The temperature, relative humidity and precipitation data were recorded three times a day during the exposure period. The mean temperature, humidity and precipitation for day 1 were 32±1° C., 75±0.58% and 0 mm, respectively. The 5 day mean temperature, humidity and precipitation of the bait exposure were 35±0.58° C., 77.67±0.88% and 0 mm, respectively. After having been exposed to the environment, the baits were used to determine their toxicity to the fire ants.

Method of Evaluating the Efficacy of Environmentally Stressed T-Bait (Cypermethrin) and Environmentally Stressed C-Bait in the Laboratory The method of evaluating the efficacy in the laboratory was the same as Example 2, but the T-bait (Cypermethrin) and C-bait were replaced with environmentally stressed T-bait (0.128% Cypermethrin) and environmentally stressed C-bait, respectively.

Result

The number of fire ants killed by one day stressed T-bait was significantly higher than for the one day stressed C-bait at 12, 48, 96 and 192 HAT. However, the number of fire ants killed by one day stressed T-bait or C-bait was not significantly different at 24 HAT. The number of fire ants killed by one day stressed T-bait or C-bait was significantly higher than the control during all the observations. For the final observation at 192 HAT, the total number of fire ants killed by one day stressed T-bait were highest at (53.62±2.14%) which was 27.36% and 96.74% more than for the one day stressed C-bait and control, respectively (F=144.88, P=0.001). The $LT_{50}$ of one day stressed T-bait and C-bait were 4.13 and 7.27 d, respectively (Table 3).

TABLE 3

Mean number of fire ant workers killed by 1 day stressed T-bait (0.128% cypermethrin), C-bait (0.045% indoxacarb) and control

| Time (H) | T-bait (Mean ± SE)[a] | C-bait (Mean ± SE)[a] | Control (Mean ± SE)[a] |
|---|---|---|---|
| 12 | 10.01 ± 1.63a | 1.58 ± 0.55b | 0 ± 0b |
| 24 | 30.60 ± 6.62a | 18.09 ± 4.79a | 0 ± 0b |
| 48 | 44.45 ± 3.47a | 32.39 ± 3.67b | 1.25 ± 0.95c |
| 96 | 52.78 ± 2.86a | 37.7 ± 3.52b | 1.75 ± 1.11c |
| 192 | 53.62 ± 2.14a | 38.95 ± 3.66b | 1.75 ± 1.11c |
| $LT_{50}$[b] | 4.13 | 7.27 | |

[a]Means within the same row followed by the same letter are not significantly different (P < 0.05) using SNK test of SAS (2008).
[b]$LT_{50}$ values (in days) were determined by probit analysis (StatPlus, 2008).

Similarly, the number of fire ants killed by five day stressed T-bait were significantly higher than by the five day stressed C-bait at 12, 24, 48, 96 and 192 HAT. The number of fire ants killed by five day stressed T-bait or C-bait were significantly higher than the control during all the observations. At the final observation at 192 HAT, the total number of fire ants killed by five day stressed T-bait were highest at (27.92±2.39%) which was 40.58% and 93.73% more than the five day stressed C-bait and control, respectively (F=30, P=0.001). The $LT_{50}$ of the 5 day stressed T-bait and C-bait were 16.62 and 29.7 d, respectively (Table 4).

TABLE 4

Mean number of fire ant workers killed by 5 day stressed T-bait (0.128% cypermethrin), C-bait (0.045% indoxacarb) and control

| Time (H) | T-bait (Mean ± SE)[a] | C-bait (Mean ± SE)[a] | Control (Mean ± SE)[a] |
|---|---|---|---|
| 12 | 5.83 ± 1.95a | 0.67 ± 0.39b | 0 ± 0b |
| 24 | 13.75 ± 3.41a | 5.32 ± 1.63b | 0 ± 0c |
| 48 | 20.62 ± 4.89a | 10.81 ± 1b | 1.25 ± 0.95c |
| 96 | 26.46 ± 2.87a | 16.24 ± 3.76b | 1.75 ± 1.11c |
| 192 | 27.92 ± 2.39a | 16.59 ± 3.58b | 1.75 ± 1.11c |
| $LT_{50}$[b] | 16.62 | 29.7 | |

[a]Means within the same row followed by the same letter are not significantly different (P < 0.05) using SNK test of SAS (2008).
[b]$LT_{50}$ values (in days) were determined by probit analysis (StatPlus, 2008).

When comparing the efficacy of normal T-bait, wet T-bait, and one and five day stressed T-baits, it was found that the number of fire ants killed by normal T-bait was significantly higher than those killed by wetted T-bait, or one and five day stressed T-baits during all of the observations, except for the 12 HAT (F=1.03, P=0.42). However, the number of fire ants killed by wet T-bait and one day environmentally stressed T-bait was not significantly different at 24, 48, 96 and 192 HAT. The normal T-bait killed all the fire ants at 96 HAT; however, wet T-bait, one and five day stressed T-bait killed only 70.62%, 53.63% and 27.92% of the fire ants at 192 HAT (Table 5).

TABLE 5

Mean number of fire ant workers killed by normal, wet, 1 and 5 day stressed T-bait (0.128% cypermethrin)

| | | | Stressed bait (day) | |
|---|---|---|---|---|
| Time (H) | Normal bait (Mean ± SE)[a] | Wet bait (Mean ± SE)[a] | 1 (Mean ± SE)[a] | 5 (Mean ± SE)[a] |
| 12 | 23.72 ± 15.17a | 5.65 ± 2.52a | 10.01 ± 1.63a | 5.83 ± 1.95a |
| 24 | 81.16 ± 7.82a | 41.60 ± 5.94b | 30.60 ± 6.62b | 13.75 ± 3.41c |
| 48 | 97.25 ± 2.75a | 60.15 ± 4.01b | 44.45 ± 3.47b | 20.62 ± 4.89c |
| 96 | 100 ± 0a | 69.71 ± 3.10b | 52.78 ± 2.86b | 26.46 ± 2.87c |
| 192 | 100 ± 0a | 70.62 ± 2.94b | 53.62 ± 2.14b | 27.92 ± 2.39c |
| $LT_{50}$[b] | 0.69 | 2.1 | 4.13 | 16.62 |

[a]Means within the same row followed by the same letter are not significantly different (p < 0.05) using SNK test of SAS (2008).
[b]$LT_{50}$ values (in days) were determined by probit analysis (StatPlus, 2008).

When comparing the efficacy of normal C-bait, wet C-bait, one and five day stressed C-baits it was found that the number of fire ants killed by normal C-bait was significantly higher than that for wet C-bait or one and five day stressed baits during all the observations, except for 12 HAT (F=1.51, P=0.25). However, at 24 HAT, the number of fire ants killed by wet C-bait, and one and five day stressed C-baits was not significantly different. Similarly, five day stressed C-bait killed a significantly less number of fire ants than wet C-bait or 1 day stressed T-bait at 48, 96 or 192 HAT. Normal C-bait killed all the ants at 96 HAT, however, wet C-bait, and one and five day stressed C-baits killed only 39.68%, 38.95% and 16.59% fire ants at 192 HAT (Table 6).

TABLE 6

Mean number of fire ant workers killed by normal, wet, 1 and 5 day stressed C-bait (0.045% indoxacarb)

| | | | Stressed bait (day) | |
|---|---|---|---|---|
| Time (H) | Normal bait (Mean ± SE)[a] | Wet bait (Mean ± SE)[a] | 1 (Mean ± SE)[a] | 5 (Mean ± SE)[a] |
| 12 | 25.72 ± 18.29a | 6.13 ± 2.42a | 1.58 ± 0.55a | 0.67 ± 0.39a |
| 24 | 75.03 ± 9.4a | 17.48 ± 2.99b | 18.09 ± 4.79b | 5.32 ± 1.63b |
| 48 | 99 ± 1a | 30.37 ± 1.74b | 32.39 ± 3.67b | 10.81 ± 1c |
| 96 | 100 ± 0a | 37.45 ± 1.30b | 37.7 ± 3.52b | 16.24 ± 3.76c |
| 192 | 100 ± 0a | 39.68 ± 2.85b | 38.95 ± 3.66b | 16.59 ± 3.58c |
| $LT_{50}$[b] | 0.74 | 8.22 | 7.27 | 29.7 |

[a]Means within the same row followed by the same letter are not significantly different (p < 0.05) using SNK test of SAS (2008).
[b]$LT_{50}$ values (in days) were determined by probit analysis (StatPlus, 2008).

Example 5

Efficacy of T-Bait and C-Bait in the Field

Method of Evaluating the Efficacy T-Bait (Cypermethrin) and C-Bait in the Field

The field experiments were conducted at the Singwu area in Taoyuan County, Taiwan. The experiment area contained only grasses. A total of 56 active fire ant colonies were selected randomly; 7 mounds were used for C-bait or T-bait and sprayed with 0 mL, 100 mL, 300 mL DD water after they were sprayed with fire ant baits, control-1 (T-bait blank, 0% cypermethrin AI) and control-2 (no bait or do nothing) for each. Baits (ca. 60 mL) were sprayed within a 50 cm radius from the center of the nest as described by some scholars (Furman et al., Sociobiology 48: 101-116, 2006 and Oi, D. H. et al., J. Econ. Entomol. 99: 1739-1748, 2006). The sprayed 0 mL, 100 mL, 300 mL DD water represented 0 ml, 0.5±0.03 ml and 1.4±0.1 ml rainfall, respectively.

One day before treatment, each nest was surveyed to determine if the colony was active or not and the size of the ant colony. The number of active nests on the field was determined on the day the baits were applied and on day 3, 5, 7, 12, 16, 23, 30 and 37 after treatment (DAT). Nests were designated as active when at least 20 adult fire ants exited the mounds of excavated soil when probed with a metal rod (4.8 mm in diameter). Treatment evaluations were based on the $LT_{50}$ (StatPlus, 2008), PHREG Procedure (SAS, 2008) and percentage of reduction in active fire ant nests relative to the initial number of treated active nests. On the day of the bait application, the field temperature, RH and wind speed were 25.18±2.5° C., 65.60±3.23%, and 10.32±1.38 km/h, respectively.

Result

A total of seven fire ant colonies were used to test each bait (T-bait and C-bait) with or without water application to determine the efficacy of baits in the field. At the end of the study (37 day) the percentage of the fire ant colonies reduced by T-bait with 0 mL, 100 mL and 300 mL water application was 85.71%, however, the speed of the reduction of the field colonies differed. The T-bait without water (0 mL) reduced 85.71% of fire ant colonies at three DAT; however, T-bait with 100 mL or 300 mL water reduced only 57.14% or 42.86% of the fire ant's colonies at three DAT. Although the field colonies reductions were different at three DAT, from five DAT till the end of the study, the T-bait with 0 mL, 100 mL and 300 mL water reduced 85.71% of the fire ant colonies (FIG. 1).

At the end of the study (37$^{th}$ day) the percentage of fire ant colonies reduced by C-bait with 0 mL, 100 mL and 300 mL water were 85.71%, 42.86% and 28.57%, respectively. At three DAT, 71.41%, 42.86% and 0% of the fire ant colonies were reduced by C-bait with 0 mL, 100 mL and 300 mL, respectively. Similarly, at five DAT, C-bait with 0 mL, 100 mL and 300 mL water reduced only 85.71%, 42.86% and 14.28% of the fire ant colonies, respectively. From 5 to 30 DAT, the percentage of the fire ant field colonies reduction remained unchanged. However, for C-bait with 300 mL at 37 DAT, the percentage of fire ant colonies reduction increased to 28.57% (FIG. 1).

The results from the PHREG analysis (SAS, 2008) revealed that the reduction of the number of fire ant colonies was not significantly different when comparing T-bait without water application with T-bait with 100 mL water application (Q=0.08, P=0.76) or 300 mL (Q=0.29, P=0.58). Similarly, the number of fire ant colonies reduced was not significantly different when comparing T-bait with 100 mL water application with T-bait with 300 mL (Q=0.04, P=0.83) or C-bait with 100 mL water application (Q=0.3, P=0.86). However, the number of fire ant colonies reduced was significantly different when comparing T-bait with 300 mL water application with C-bait with 300 mL water application (Q=3.88, P=0.04) (Table 7).

Similarly, the number of fire ant colonies reduced were not significantly different when comparing C-bait without water application with T-bait without water application (Q=0.01, P=0.92), however, the number of fire ant colonies reduced were significantly different when C-bait without water application was compared with C-bait with 300 mL water application (Q=4.15, P=0.04). Furthermore, the number of fire ant colonies reduced were significantly different when C-bait with 300 mL water application was compared with C-bait with 100 mL water application (Q=4.15, P=0.04) (Table 7).

A positive correlation between the amount of water applied to the bait and the $LT_{50}$ for the number of fire ant field colonies reduced was observed. When the amount of water applied was increased from 0 mm to 100 mL or 300 mL, the $LT_{50}$ of T-bait was also increased from 2.12 to 3.01 or 3.49 d, respectively and for C-bait from 2.56 to 33.98 or 243.99 d, respectively (Table 7).

TABLE 7

Effect of water on the reduction of fire ant field colonies by T-bait (0.128% cypermethrin) and, C-bait (0.045% indoxacarb)

| Source | | T-bait (P-value)$^a$ | | | C-bait (P-value)$^a$ | | |
|---|---|---|---|---|---|---|---|
| | | 0 mL | 100 mL | 300 mL | 0 mL | 100 mL | 300 mL |
| T-bait | 0 mL | | 0.76 | 0.58 | | | |
| | 100 mL | | | 0.83 | | 0.86 | |
| | 300 mL | | | | | | 0.04 |
| C-bait | 0 mL | 0.92 | | | | | 0.04 |
| | 100 mL | | | | 1 | | |
| | 300 mL | | | | | 0.04 | |
| $LT_{50}$$^b$ | | 2.12 | 3.01 | 3.49 | 2.56 | 33.98 | 243.99 |

$^a$P values were determined by the PHREG Procedure (SAS, 2008).
$^b$$LT_{50}$ values (in days) were determined by probit analysis (StatPlus, 2008).

Example 6

Compatibility of the T-Carrier with Other Commercial Toxicants

T-carrier with Other Commercial Toxicants to Produce Bait

D-althrin (90%), cypermethrin (94%), permenthrin (92%) and pyrethrin (20%) were obtained from Chung Shi Chemical Plant, Hsinchu, Taiwan.

The same procedure as described above was applied to formulate T-bait with the four commercial toxicants, d-althrin, cypermethrin, permenthrin and pyrethrin, respectively. For each toxicant, T-bait with four different concentrations (0.002% 0.008%, 0.032% and 0.128%) were formulated. Therefore, a total of 15 T-bait formulations, d-althrin [0.002% (A1), 0.008% (A2), 0.032% (A3) and 0.128% (A4)], cypermethrin [0.002% (C1), 0.008% (C2), 0.032% (C3)], permenthrin [0.002% (P1), 0.008% (P2), 0.032% (P3) and 0.128% (P4)], and pyrethrin [0.002% (PY1), 0.008% (PY2), 0.032% (PY3) and 0.128% (PY4)] were formulated for the evaluation and comparison with the commercial fire ants bait, Advion and Conserve.

Method of Evaluating the Efficacy of T-Bait with Different Toxicants in the Laboratory The method of evaluating the efficacy in the laboratory was the same as Example 2, but the T-bait (Cypermethrin) was replaced by T-bait with different toxicants.

Similarly, after formulating T-baits with different concentrations of toxicants, the efficacy of T-bait against fire ants was compared with commercial fire ant bait, Conserve (spinosad 0.015%) and Advion (indoxacarb 0.045%). This study was replicated five times, with ants from a separate colony being used for each replicate.

Result

Besides cypermethrin (0.128%) formulated T-baits, the efficacy of T-bait was also evaluated using four different commercial toxicants: d-althrin, permenthrin pyrethrin and cypermethrin with different concentrations (C1, C2 and C3). The results from the experiments reveal that all four toxicants were compatible with the T-carrier showing different efficacies against fire ants under laboratory conditions.

At the end of the study (192 HAT), T-bait with cypermethrin 0.008% (C2) and 0.032% (C3), permenthrin 0.032% (P3) and 0.128% (P4) and pyrethrin 0.128% (PY4) had killed more than 50% of the fire ants. T-bait with d-althrin (0.128%) killed 44.4% of fire ants but failed to reach 50%.

At 12 HAT, a significantly higher number of fire ants were killed by T-bait (P=0.001, F=5.56, df=10) than by the other baits, however, the number of fire ants killed by Conserve and T-bait or Conserve, C2, C3 and P4 or T-bait, C-bait, C2, C3, P3, P4 and PY4 were not significantly different (Table 8).

Similarly, at 24 and 48 HAT, a significantly higher number of fire ants were killed by C4 than by the other baits, however, the number of fire ants killed by T-bait, C3, P4, C-bait and Conserve or C2, C3, P3, P4, PY4, and C-bait were not significantly different (Table 8).

Furthermore, at 96 and 192 HAT, a significantly higher number of fire ants were killed by T-bait, Conserve and C-bait than by the other baits, however, the number of fire ants killed by T-bait, Conserve, C-bait, C3, P4 and Conserve or C2, C3, P3, P4 and PY4 were not significantly different. At 96 HAT, T-bait, Conserve and C-bait killed 100% of the ants (Table 8).

TABLE 8

Mortality rate of fire ant workers by seven different formulations of T-baits and two commercial fire ant baits under laboratory conditions

| Baits[b] | 12H (Mean ± SE)[a] | 24H (Mean ± SE)[a] | 48H (Mean ± SE)[a] | 96H (Mean ± SE)[a] | 192H (Mean ± SE)[a] | $LT_{50}$[b] |
|---|---|---|---|---|---|---|
| Conserve | 85.48 ± 4.59ab | 96.11 ± 2.35a | 100 ± 0a | 100 ± 0a | 100 ± 0a | 0.31 |
| T-bait | 23.71 ± 15.32c | 81.15 ± 7.82ab | 97.25 ± 2.75ab | 100 ± 0a | 100 ± 0a | 0.34 |
| Advion | 25.72 ± 18.29c | 75.032 ± 9.40ab | 99 ± 1ab | 100 ± 0a | 100 ± 0a | 0.71 |
| T-bait C2 | 42.16 ± 19.59bc | 47.69 ± 20.55b | 51.4 ± 20.03b | 53 ± 19.33b | 53 ± 19.34b | 1.61 |
| T-bait C3 | 52.37 ± 17.40bc | 58.33 ± 16.25ab | 61.75 ± 16.24ab | 63.57 ± 15.87ab | 63.78 ± 15.83ab | 0.93 |
| T-bait P3 | 29.8 ± 11.07c | 41 ± 12.76b | 51 ± 13.47b | 51.8 ± 13.79b | 52.6 ± 13.38b | 2.41 |
| T-bait P4 | 38.16 ± 12.69bc | 59.27 ± 9.88ab | 70.23 ± 8.33ab | 71.63 ± 7.82ab | 72.6 ± 7.6ab | 0.9 |
| T-bait PY4 | 31 ± 14.59c | 44.6 ± 12.97b | 51.4 ± 12.91b | 52 ± 13.05b | 53.8 ± 12.66b | 2.61 |
| T-bait blank | 0 ± 0d | 0.4 ± 0.4c | 0.4 ± 0.4c | 1 ± 0.45c | 1.8 ± 0.49c | n/a |
| No bait | 0 ± 0d | 0 ± 0c | 1.2 ± 0.73c | 1.6 ± 0.87c | 1.6 ± 0.87c | n/a |
| P | 0.0001 | 0.0001 | 0.0001 | 0.0001 | 0.0001 | |
| F | 5.5.6 | 9.32 | 12.39 | 12.97 | 13.16 | |
| DF | 10 | 10 | 10 | 10 | 10 | |

[b]C = cypermethrin, P = permethrin, PY = pyrethrin, 2 = 0.008% ai, 3 = 0.032% ai, and 4 = 0.128% ai
[a]Means within the same column followed by the same letter are not significantly different (P < 0.05) using SNK test of SAS (2008).
[b]$LT_{50}$ values (in days) were determined by probit analysis (StatPlus, 2008).

What is claimed is:

1. A water resistant and anti-oxidant bait formula, consisting of:
   (a) an effective amount of toxicant,
   (b) an attractant consisting of an oil,
   (c) shrimp shell powder, and
   (d) distiller's dried grains with solubles (DDGS) as a carrier.

2. The bait formula of claim 1, wherein the toxicant is d-Allethrin, cypermethrin, permethrin or pyethrin.

3. The bait formula of claim 1, wherein the toxicant is cypermethrin.

4. The bait formula of claim 3, wherein the cypermethrin having an effective amount of 0.128%.

5. The bait formula of claim 1, wherein the oil is soybean oil.

6. The bait formula of claim 1, wherein the bait having a weight ration of shrimp shell powder to DDGS from 1:10 to 2:9.

7. The bait formula of claim 1, wherein the bait having a weight ration of shrimp shell powder to DDGS is 1:5.

8. The bait formula of claim 1, wherein the attractant is 15% by weight in the bait.

9. The bait formula of claim 1, wherein the shrimp shell powder is 20% by weight in the bait.

10. The bait formula of claim 1, wherein the ant is a fire ant.

* * * * *